United States Patent
Matthewson et al.

(10) Patent No.: US 11,266,347 B2
(45) Date of Patent: Mar. 8, 2022

(54) APPARATUS AND METHOD FOR PRODUCING A FLOW PROFILE

(71) Applicant: Novartis AG, Basel (CH)

(72) Inventors: Peter Matthewson, Cambridgeshire (GB); Laure Mahé, Cambridgeshire (GB)

(73) Assignee: Novartis AG, Basel (CH)

( * ) Notice: Subject to any disclaimer, the term of this patent is extended or adjusted under 35 U.S.C. 154(b) by 472 days.

(21) Appl. No.: 15/545,375

(22) PCT Filed: Jan. 22, 2016

(86) PCT No.: PCT/EP2016/051389
§ 371 (c)(1),
(2) Date: Jul. 21, 2017

(87) PCT Pub. No.: WO2016/116629
PCT Pub. Date: Jul. 28, 2016

(65) Prior Publication Data
US 2018/0008192 A1 Jan. 11, 2018

(30) Foreign Application Priority Data
Jan. 23, 2015 (EP) .................................. 15152410

(51) Int. Cl.
*A61M 15/00* (2006.01)
*A61B 5/087* (2006.01)
(Continued)

(52) U.S. Cl.
CPC ............ *A61B 5/4833* (2013.01); *A61B 7/003* (2013.01); *A61M 15/00* (2013.01);
(Continued)

(58) Field of Classification Search
CPC ....... A61B 5/4833; A61B 7/003; A61B 5/087; G01F 1/666; A61M 2205/3375; A61M 15/0065
(Continued)

(56) References Cited

U.S. PATENT DOCUMENTS 6,178,302 B1 1/2001 Nagashima et al.
6,958,691 B1 10/2005 Anderson et al.
(Continued)

FOREIGN PATENT DOCUMENTS

EP 2686049 B1 3/2015
EP 2859906 4/2015
(Continued)

OTHER PUBLICATIONS

Holmes, Martin s. et al., 'A Method of Estimating Inspiratory Flow Rate and Volume from an Inhaler using Acoustic Measurements', IOP Publishing, Physiol. Meas. 34, 2013, pp. 903-914 (Year: 2013).*

(Continued)

*Primary Examiner* — Bradley H Philips
*Assistant Examiner* — Savannah L Gabriel
(74) *Attorney, Agent, or Firm* — Luedeka Neely Group, P.C.

(57) ABSTRACT

A method for generating a flow profile of an inhalation device is described. The method comprises the step of measuring acoustic emissions induced by inhalation flow through the inhalation device. The method further comprises the step of detecting peak frequencies in the measured acoustic emissions and generating a flow profile based on the detected peak frequencies. A corresponding device is also described.

16 Claims, 6 Drawing Sheets

(51) Int. Cl.
*A61B 5/00* (2006.01)
*A61B 7/00* (2006.01)

(52) U.S. Cl.
CPC ......... *A61M 15/0065* (2013.01); *A61B 5/087* (2013.01); *A61M 2205/3334* (2013.01); *A61M 2205/3375* (2013.01); *A61M 2205/3584* (2013.01); *A61M 2205/52* (2013.01); *A61M 2230/40* (2013.01)

(58) Field of Classification Search
USPC ....................................................... 600/538
See application file for complete search history.

(56) References Cited

U.S. PATENT DOCUMENTS

| | | | |
|---|---|---|---|
| 7,151,456 | B2 | 12/2006 | Godfrey |
| 7,191,777 | B2 | 3/2007 | Brand et al. |
| 7,721,730 | B2 | 5/2010 | Hamano et al. |
| 8,251,914 | B2 | 8/2012 | Daniels et al. |
| 8,424,517 | B2 | 4/2013 | Sutherland et al. |
| 8,474,452 | B2 | 7/2013 | Gumaste |
| 8,479,730 | B2 | 7/2013 | Ziegler et al. |
| 8,622,241 | B2 | 1/2014 | Geboers et al. |
| 8,807,131 | B1 | 8/2014 | Tunnell et al. |
| 9,016,147 | B2 | 4/2015 | Adamo |
| 9,242,056 | B2 | 1/2016 | Andersen |
| 9,390,457 | B2 | 7/2016 | Baym et al. |
| 9,555,200 | B2 | 1/2017 | Hosemann et al. |
| 9,744,319 | B2 | 8/2017 | Denyer et al. |
| 10,029,056 | B2 | 7/2018 | Reilly |
| 10,463,816 | B2 | 11/2019 | Oliveras et al. |
| 2002/0189615 | A1 | 12/2002 | Henry |
| 2003/0074223 | A1 | 4/2003 | Hickle et al. |
| 2004/0025877 | A1 | 2/2004 | Crowder |
| 2005/0087473 | A1 | 4/2005 | Fabricius |
| 2008/0110452 | A1 | 5/2008 | Kotnik |
| 2009/0308387 | A1 | 12/2009 | Andersen et al. |
| 2011/0298587 | A1 | 12/2011 | Walz |
| 2012/0003928 | A1 | 1/2012 | Geboers |
| 2012/0247235 | A1 | 10/2012 | Adamo et al. |
| 2013/0146613 | A1 | 6/2013 | Balthes |
| 2013/0151162 | A1* | 6/2013 | Harris ................... A61M 15/00 702/19 |
| 2014/0106324 | A1* | 4/2014 | Adams ................ A61M 15/009 434/262 |
| 2014/0182854 | A1 | 7/2014 | Mukhopadhyay |
| 2015/0174349 | A1 | 6/2015 | Tunnell et al. |
| 2015/0196724 | A1 | 7/2015 | Adamo et al. |
| 2015/0196728 | A1 | 7/2015 | Aldana |
| 2016/0081651 | A1* | 3/2016 | Nam ...................... A61B 7/003 600/529 |
| 2016/0256639 | A1 | 9/2016 | Van Sickle |

FOREIGN PATENT DOCUMENTS

| | | |
|---|---|---|
| JP | 2006153760 A | 6/2006 |
| JP | 2009001326 A | 1/2009 |
| JP | 2010-160230 | 7/2010 |
| JP | 2011-174788 | 9/2011 |
| RU | 2372105 C2 | 11/2009 |
| WO | 1992/017231 | 10/1992 |
| WO | 2003/020349 | 3/2003 |
| WO | 2005113042 A1 | 12/2005 |
| WO | 2007/101438 | 9/2007 |
| WO | 2010/066456 | 6/2010 |
| WO | 2011/56889 | 5/2011 |
| WO | 2011/130583 | 10/2011 |
| WO | 2012/123448 | 9/2012 |
| WO | 2013016784 A1 | 2/2013 |
| WO | 2014033229 A1 | 3/2014 |
| WO | 2014/204511 | 12/2014 |
| WO | 2015/127258 | 8/2015 |

OTHER PUBLICATIONS

Search Report and Written Opinion for PCT/EP2016/051389, 15 pages.
CNIPA examination report for CN app. No. No. 201680046268.6, dated Mar. 9, 2020, 9 pages.
English translation of JP Office Action for JP app. No. 2017-567301, dated Mar. 3, 2019, 8 pages.
EPO Examination Report for EP app. No. 15175216.9, dated Aug. 7, 2018,4 pages.
EPO Examination Report for EP app.No. 15175216.9, dated Apr. 3, 2020, 5 pages.
EPO Search Report for EP app. No. 15 175216., dated Sep. 24, 2015, 5 pages.
JP Office Action for JP app. No. 2017-567301, dated Mar. 3, 2019, 6 pages.
RU Official Action for RU app. No. 2018103754/14, dated Jan. 31, 2019, 5 pages.
RU Search Report for RU app. No. 2018103754/14, dated Jan. 29, 2019, 2 pages.
USPTO Notice of References Cited for U.S. Appl. No. 15/545,375, dated Oct. 14, 2020, 1 page.
BR Examination Report—dated May 12, 2020—No. BR112017028579-7.
EPO Examination Report—dated Jul. 2020—No. 16741882.1.
Holmes, Physiological Measurements 34:903-914, 2013.
Coates, "Influence of air flow on the performance of a dry powder inhaler using computational and experimental analyses" Pharm Res. 22(9):1445-53, Sep. 2005.
Coates, "The role of capsule on the performance of a dry powder inhaler using computational and experimental analyses" Pharm Res. 22(6):923-32, Jun. 2005.
CNIPA examination report dated Jan. 19, 2021 No. 201680046268.6.
CNIPA examination report dated Jul. 2021 No. 201680046268.6.
EPO Communication—dated Apr. 9, 2021—No. 15175216.9.

* cited by examiner

Calibration data

Time series trace

Spectrogram of inhalation

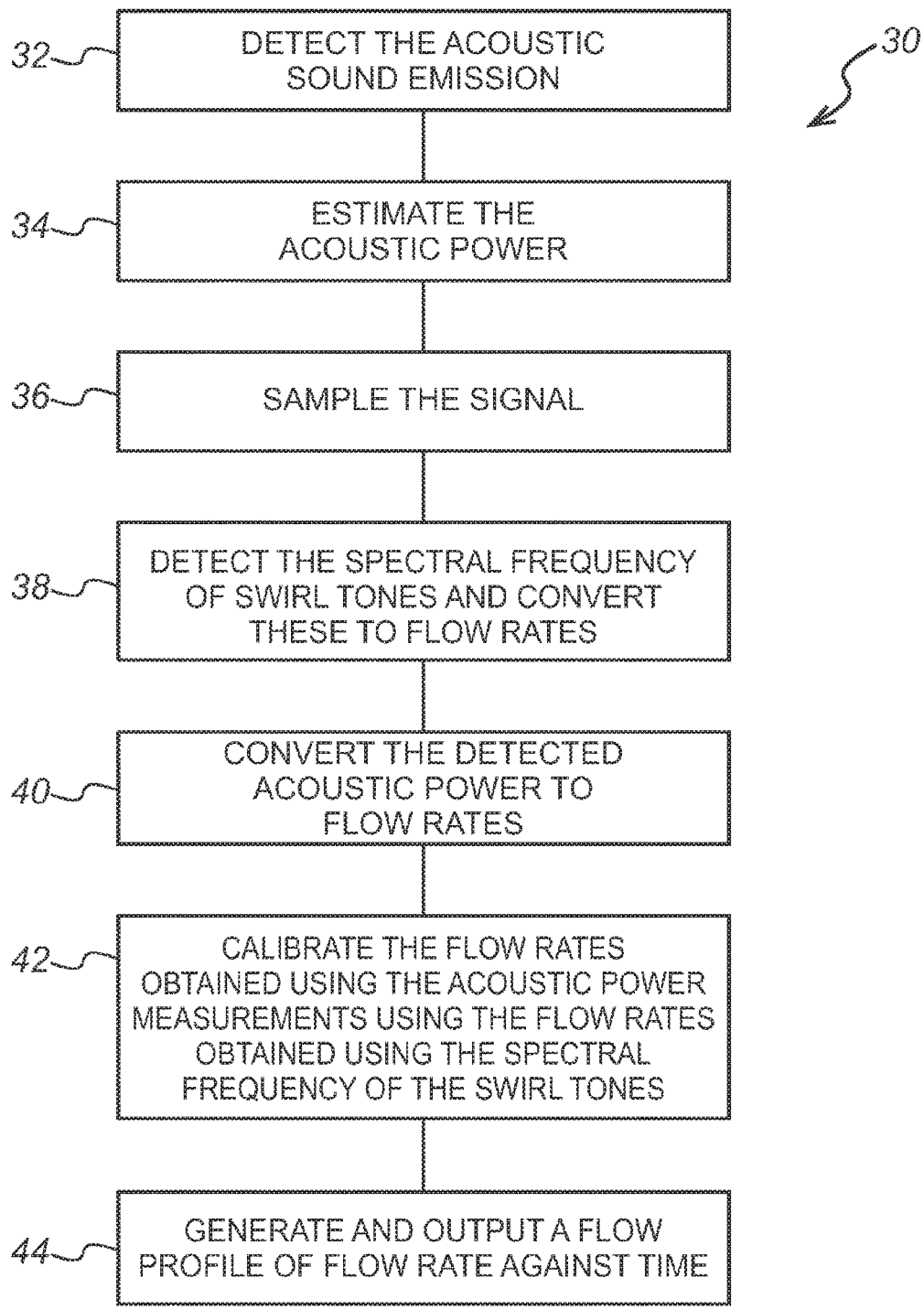

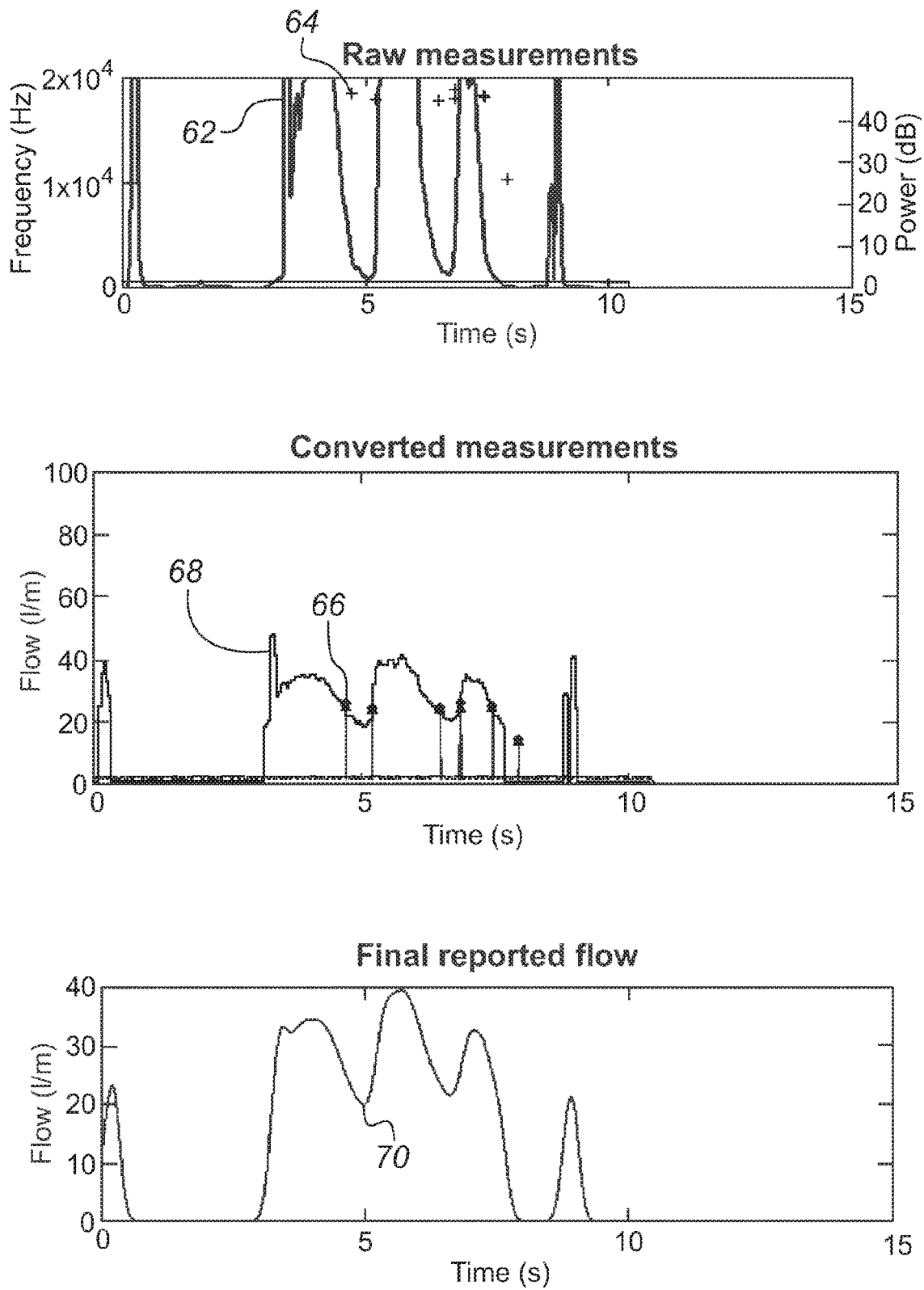

APPARATUS AND METHOD FOR PRODUCING A FLOW PROFILE

This application is a Section 371 national phase entry of PCT application PCT/EP2016/051389, filed Jan. 22, 2016. This application also claims the benefit of the earlier filing date of European patent application 15152410.5, filed Jan. 23, 2015.

The invention relates to an apparatus and a method for producing a flow profile. In particular, the invention relates to an apparatus and method for producing a flow profile of an inhalation device, such as an inhaler.

BACKGROUND

Inhaler devices are used in the medical industry to administer drugs as a powder or using an aerosol, for example. The effectiveness of the drug administration may be dependent on how the device is used, which may be related to a flow rate or flow profile that is achieved by a user of the inhaler. Accordingly, it is desirable to measure an inspiratory flow rate as a function of time (i.e., a flow profile) for a patient using an inhaler device. Such a measurement can be used, for example, to support clinical trials to assess the breathing style of the participants of the trails, and for measuring the usage of the inhaler device during trials to assist in evaluating device usage effectiveness. The measurements may also be used to train users in how to use the inhaler according to an inhalatory profile in accordance with effective usage of the device, during supervised or unsupervised training, for example. The inhalation measurement may produce assessments and corrective suggestions for the user. Moreover, adherence monitoring could also be achieved by producing a flow profile, since it is potentially useful to use inhalatory flow measurements as part of a system used by medical practitioners that wish to evaluate adherence to a course of treatment.

It is known to estimate flow rate by measuring the audio power present in a selected frequency band in the audio spectrum. The power measured in this selected frequency band is then converted to a flow rate using a previously determined calibration table, which includes values of measured audio power within a filtered bandwidth and known flow rates.

To use this known method successfully, there are a number of factors to control, such as the propagation path for the signal from an inhaler device, for example, to a microphone, and the gain and the sensitivity of the microphone and associated soundcard may also vary. Together these factors can limit the accuracy of the final flow rate estimate. To mitigate these variable factors, the microphone may typically be a high quality repeatable device, which is attached to the inhaler to reduce the variations in propagation path and coupling.

Generally, it is desirable to make the flow measurements with as little disturbance to the user as possible and with a minimum amount of modification/additional apparatus. Accordingly, there is a desire to improve this method of obtaining a flow rate or flow profile from an inhaler device.

BRIEF DESCRIPTION OF THE DRAWINGS

The present disclosure can be understood with reference to the description of the embodiments set out below, in conjunction with the appended drawings in which:

FIG. 8 is a flow chart depicting a method performed by a processor of the mobile device; and FIG. 9 illustrates a series of graphs used to illustrate the method shown in the flow chart of FIG. 8 when performed using a smartphone and a general purpose computer.

DESCRIPTION

Figure 1:
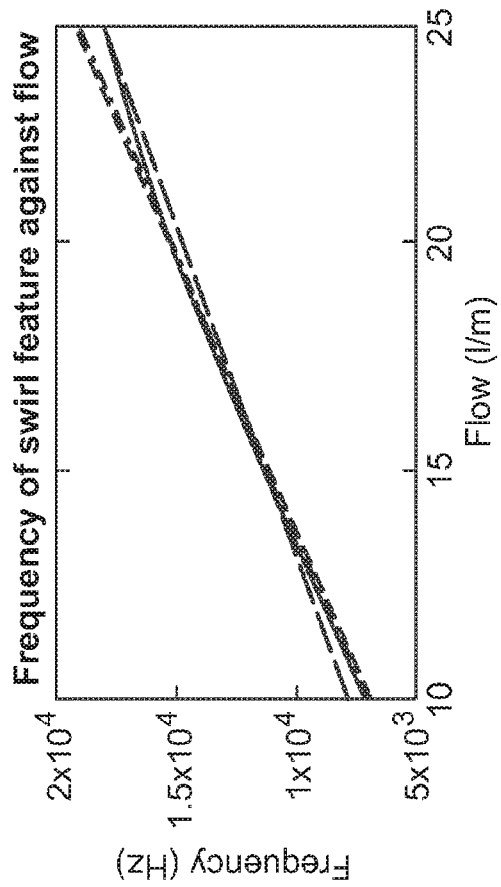
FIG. 1 is a graph illustrating a relationship between spectral peak of a swirl tone of an inhaler device and air flow rate through the inhaler device.

According to a first aspect of the invention there is provided a method for generating a flow profile of an inhalation device, comprising the steps of: measuring acoustic emissions induced by inhalation flow through the inhalation device; detecting two or more peak frequencies in the measured acoustic emissions; and generating a flow profile based on the detected peak frequencies. Therefore, it is possible to more accurately determine a flow profile for an inhalation device during use that is broadly independent on the relative proximity of the inhalation device and a measuring device (e.g., microphone).

Each of the peak frequencies may represent a spectral peak of an air flow, which may be describe as a rotating or a rotational air flow, through the inhalation device at a predetermined flow rate.

The acoustic emissions may be measured over a predetermined period of time and the two or more peak frequencies are detected at regular intervals over the predetermined period of time.

The flow profile may be generated using a predetermined relationship between the two or more peak frequencies and respective flow rates through the inhalation device, and the predetermined relationship may be represented by a look-up table.

The method may further comprise detecting acoustic power of the measured acoustic emissions and generating the flow profile based on the detected acoustic power and the detected peak frequencies.

According to a second aspect of the invention there is provided a method for generating a flow profile of an inhalation device, comprising the steps of: measuring acoustic emissions induced by inhalation flow through the inhalation device; detecting one or more peak frequencies in the measured acoustic emissions; detecting acoustic power of the measured acoustic emissions; and generating a flow profile based on the detected acoustic power and the detected peak frequencies. Therefore, it is possible to more accurately determine a flow profile based on a measured audio power for an inhalation device during use that is broadly independent on the relative proximity of the inhalation device and a measuring device (e.g., microphone).

Each of the peak frequencies may represent a spectral peak of an air flow, which may be describe as a rotating or a rotational air flow, through the inhalation device at a predetermined flow rate.

The acoustic emissions may be measured over a predetermined period of time and the one or more peak frequencies and the acoustic power are detected at regular intervals over the predetermined period of time.

The flow profile may be generated using predetermined relationships between the one or more peak frequencies and respective flow rates through the inhalation device, and acoustic power and respective flow rates through the inhalation device. The predetermined relationships may be represented by a look-up table.

The acoustic power may be detected within a predetermined frequency band.

One or more flow rates of the flow profile determined based on the detected acoustic power are calibrated with respect to one or more flow rates determined based on the detected peak frequencies. Thus, it is possible to determine, or detect, a flow rate based on the detected acoustic power, which is subsequently calibrated or adjusted according to a flow rate which has been determined, or detected according to a detected peak frequency.

According to a third aspect of the invention there is provided a computer program product having instructions stored thereon which when executed on a processor performs the above-described methods.

According to a fourth aspect of the invention there is provided a method of monitoring use of an inhalation device, comprising the steps of: instructing a user to inhale air through an inhalation device; performing any one of the above-described methods as the user inhales air through the inhalation device; and storing the flow profile.

According to a fifth aspect of the invention there is provided a method of training use of an inhalation device, comprising the steps of: instructing a user to inhale air through an inhalation device; performing any one of the above-described methods as the user inhales air through the inhalation device; displaying the flow profile; determining any portions of the flow profile that require improvement; and communicating any improvements to the user.

According to a sixth aspect of the invention there is provided a device comprising: a processor in communication with a microphone, wherein the microphone is configured to detect acoustic emissions; the processor is configured to: detect two or more peak frequencies in the measured acoustic emissions; and generate a flow profile based on the detected peak frequencies.

According to a seventh aspect of the invention there is provided a device comprising: a processor in communication with a microphone, wherein the microphone is configured to detect acoustic emissions; the processor is configured to: detect one or more peak frequencies in the measured acoustic emissions; detect acoustic power of the measured acoustic emissions; and generate a flow profile based on the detected acoustic power and the detected peak frequencies.

The device may comprise a microphone, and may form part of a mobile device, such as a mobile handset or telephone. Moreover, the microphone may be integrated within the device.

Figure 2:
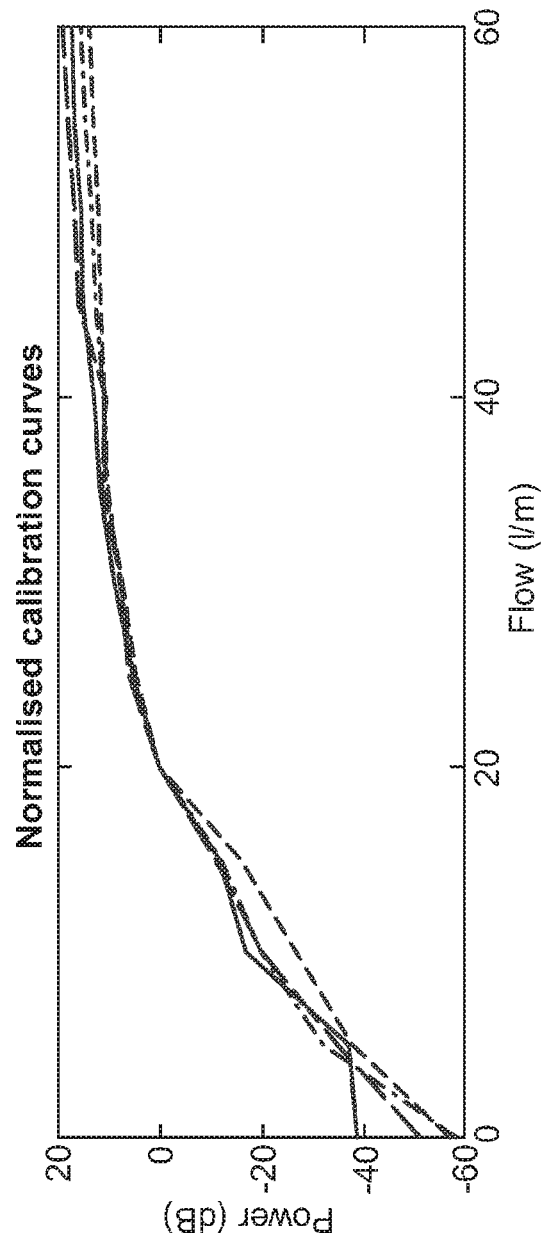
FIG. 2 is a graph of acoustic power versus flow rate of four inhalers used to obtain spectral peak frequencies.

The applicants have identified that the internal swirl motion and rapid rotation of air travelling through chambers of an inhaler used to administer a medicament causes the generation of an associated spectral peak. This swirl motion of air causes an acoustic emission which may be referred to as a swirl tone. In this regard, FIG. 1 is a graph which illustrates the relationship between the spectral peak of the swirl tone and the air flow rate through a powder type inhaler. It will be appreciated that the method described herein may be applied to any form of inhalation device, and more specifically to an inhalation device that utilises the movement of inhaled air, or an air flow, to administer a medicament to a user. More specifically the method may be applied to a power-type inhalation device that includes various passageways through which air passes when inhaled. The graph in FIG. 1 illustrates the measured frequency of the spectral peak against a known flow rate which was applied to the inhalers. Four inhalers were tested, and the graph illustrates the results from these four different inhalers of the same type, and shows that the spectral peak measurement is consistent over the range of 10 to 25 litres per minute (approximately 0.000167 to 0.000417 $m^3/s$). This is advantageous because frequency is typically easy to measure and is believed not to depend on the losses in the acoustic propagation path from the inhaler to a microphone, and the internal conversion and translation processes. Moreover, it is possible to estimate simultaneously the acoustic power in a defined bandwidth. For example, FIG. 2 shows a graph of acoustic power versus flow rate of the four inhalers used to obtain the spectral peak frequencies. A band pass filter is used to filter the received acoustic emission signal from a microphone, and the filtered signal is normalised to 0 dB audio power at 20 litres per minute (approximately 0.0003 $m^3/s$). The band pass filter used is centred at 5 kHz and has a pass band of 8 kHz.

If it is assumed that at some stage in an inhalatory flow profile the flow rate will be within the flow range of 10 to 25 litres per minute, it is possible to utilize the spectral peaks to accurately determine a flow rate measurement, independent of the acoustic power, and to calibrate the power level of the acoustic power so that a flow profile outside of the flow range of 10 to 25 litres per minute may be obtained. Moreover, if an accumulation time for the acoustic filtering is set to a sufficiently low value (e.g., 80 milliseconds), there is a high probability that multiple spectral peaks will be detected.

Figure 3:
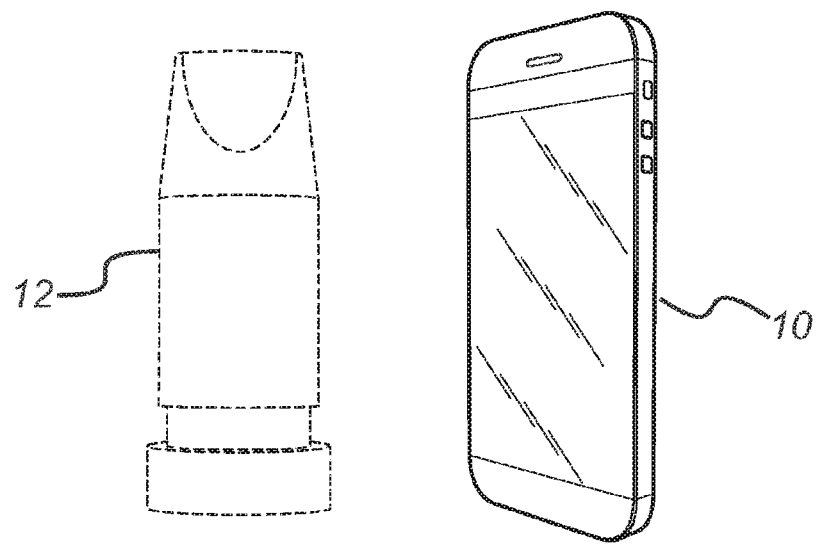
FIG. 3 shows a mobile device according to an aspect of the invention.

FIG. 3 shows a mobile device 10 according to an aspect of the invention. The mobile device 10 is preferably a mobile phone or handset, which may be referred to as a smartphone. The device 10 is illustrated in the figure as being proximal to an inhaler device 12. In the figure, the device 10 is within 0.1 m of the inhaler 12, but it will be appreciated that the device 10 and the inhaler 12 may be in contact with one another or may be spaced apart by up to 1 m. However, the distance between the device 10 and the inhaler 12 will depend on the sensitivity of a transducer (e.g., microphone) within the device 10.

Figure 4:
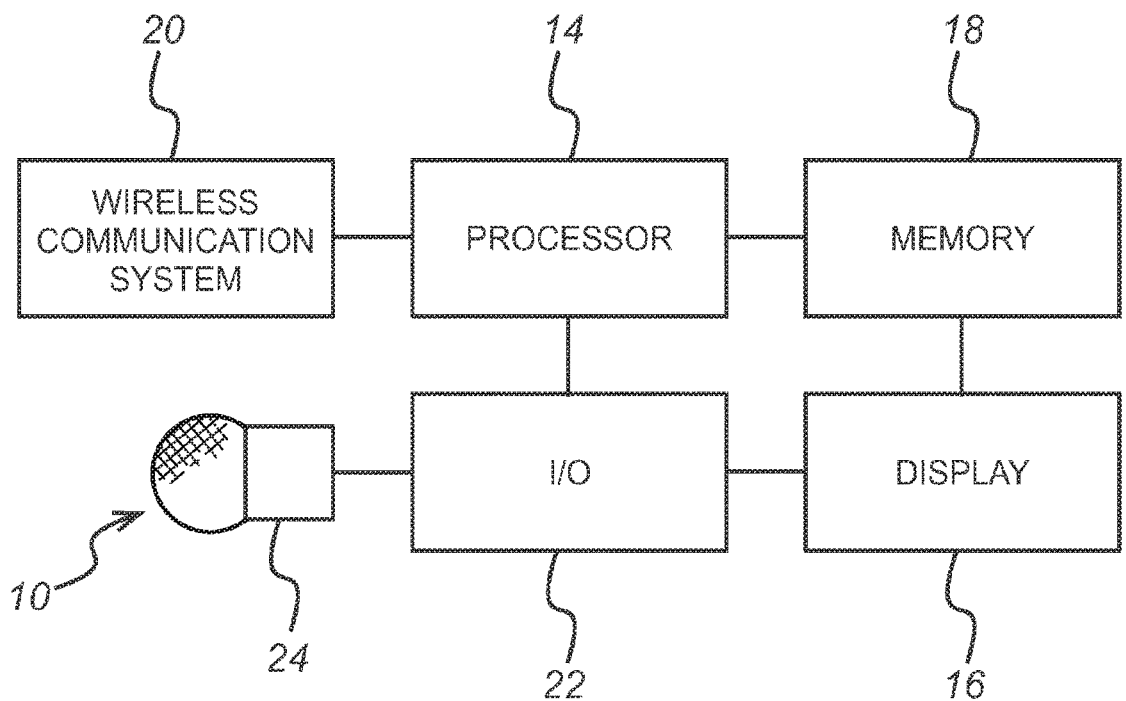
FIG. 4 illustrates the mobile device schematically.

FIG. 4 illustrates the mobile device 10 schematically. The device 10 comprises a processor 14 coupled to a display 16, memory (e.g., RAM and/or ROM) 18, a wireless communication system 20, an input/output interface 22 and a transducer 24. The processor 14 is capable of launching and running software programs (e.g., applications) stored in the memory 18 of the device 10. The processor 14 may receive data input from various sources, such as a touch-sensitive overlay on the display 16 for receiving user input, and/or the transducer 24. The transducer 24 in this example is a microphone and is the microphone that is typically used in the mobile device 10 when a user makes and receives voice calls. The wireless communication system 20 is a short-range communication system and may include a wireless bus protocol compliant communication mechanism such as a Bluetooth® communication module to provide for communication with similarly-enabled systems and devices or IEEE 802.11 radio standards, which is more typically known as WiFi. The wireless communication system also enables the device to communicate with a wireless network to provide data and voice capabilities as is well known in the art. The memory 18 data stored thereon may be used by the processor 14, and the processor 14 may store data on the memory 18, such as the results from an analysis or raw data received from an input device, for example. It will be appreciated that if device 10 is a smartphone it will include various other hardware and software components as will be known to the person skilled in the art, but which are not described herein for simplicity.

Figure 5:
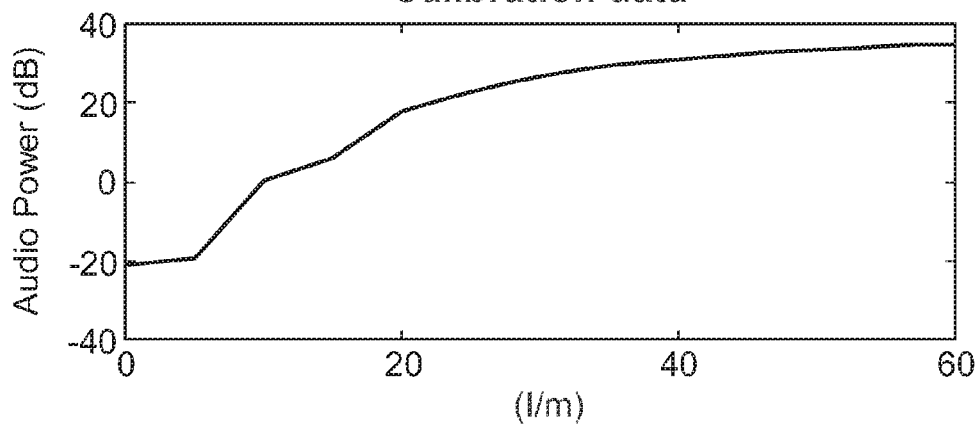
FIG. 5 illustrates a calibration curve of audio power against flow rate for an inhaler device.

A method for generating a flow profile using the spectral peak of a swirl tone in an inhaler is now described in association with FIGS. 3, 4, and 5. The method involves calibrating the inhaler device 12 using the mobile device 10 to characterise the audio properties of the inhaler device 12. This initial calibration is performed once on a test device, such that the resultant curves, expression, look-up table and/or graphs can be used with other production inhaler devices which have been manufactured according to similar processes. The initial calibration will be described in association with the mobile device 10 using an application available on the mobile device 10. However, it will be appreciated that this initial calibration may be performed on a general purpose computer.

In the initial calibration, the inhaler 12 is coupled to a suction pump (not shown) to provide a controllable air flow through the inhaler 12 to simulate it during normal use. The air flow through the inhaler device 12 is varied from 0 to 60 litres per minute (approximately 0.001 $m^3$/s), with 5 litres per minute increments (approximately 0.00008 $m^3$/s). While air flow through the inhaler device 12 is provided by the suction pump, the microphone 24 is used to detect the acoustic emission (or acoustic sound emission) produced by the inhaler 12, which is sampled by the processor 14 and stored in the memory 18. It will be appreciated that the application running on the mobile device 10 may prompt the user to begin the air flow and to terminate the sampling by the processor 14 once the air flow has been increased to its maximum value for the purpose of the calibration. The processor 14 optionally averages the power spectrum using known techniques.

For each flow rate (i.e., 5, 10, 15, 20, 25, 30, 35, 40, 45, 50, 55 and 60 litres per minute), the acoustic power is estimated by the processor 14 in a spectral width of 8 kHz at a centre frequency of 5 kHz (i.e., the sampled data for each flow rate is filtered using a band pass filter). It will be appreciated that the amplitude of the signal measured by the microphone can be converted to an acoustic power using known techniques and the properties of the microphone. The processor 14 subsequently performs regression on the acoustic power measurements to obtain an expression of power in dB against flow rate. The processor 14 may optionally cause the acoustic power measurements against flow rate to be displayed on the display 16, for example. The processor 14 may also store the obtained acoustic power measurements in a look-up table and subsequently use linear interpolation, if required, based on the data in the look-up table. FIG. 5 illustrates a calibration curve of the audio power against flow rate for the inhaler device 12.

The processor 14 subsequently detects spectral peaks in the acoustic sound emission at each of the induced flow rates in the range of 0 to 25 litres per minute (i.e., 5, 10, 15, 20, 25 litres per minute), which may be referred to as the low flow rates. As mentioned above, it was found that for a particular type of inhalation device spectral peaks were observed over a range of 10 to 25 litres per minute (approximately 0.000167 to 0.000417 $m^3$/s). However, it will be appreciated that spectral peaks may be observed at higher or lower flow rates than these. Moreover, it is understood that the spectral peaks are possibly a result of the internal swirl motion and rapid rotation of air travelling through chambers of an inhalation device. However, this may not be the case for all inhalation devices, such that other inhalation devices may exhibit spectral peaks that are not caused by the internal swirl motion and rapid rotation of air travelling through its chambers.

The spectral peak detection is obtained by a 2-dimensional background estimate using a median filter and thresholding the signal sampled by the processor 14 to identify the swirl feature when the signal exceeds the threshold by a set amount in decibels. In particular, a Fast Fourier Transform (FFT) in time is applied to the sampled signal to obtain a spectrogram. A median filter is then applied to columns of the spectrogram using a sliding window of typically 29 samples to estimate a robust background average at each time sample and frequency point. Any signal points that are greater than a certain threshold value in decibels (e.g., 20 dB) above the local median value at that point are designated to be above the threshold. The peak frequency is then taken to be the largest of the points which are greater than the threshold in a contiguous range of points over the threshold. During the calibration stage, the flow rate is kept at a constant by the suction pump, so it is typical that only a single peak frequency will be detected. It will be appreciated that other image processing techniques may be used to identify and estimate the spectral peak of the swirl tone using 2-dimensional image processing line finding or other feature extraction methods, or by Kalman filtering to track the evolution of the spectral peak in time. Once the processor 14 has obtained the spectral peak frequency at each of the low flow rates, regression is used to obtain an expression of spectral frequency against flow rate. The processor 14 may optionally display the spectral power measurements against flow rate. The processor 14 may also store the obtained spectral power measurements in a look-up table and subsequently use linear interpolation, if required, based on the data in the look-up table.

The initial calibration of the inhaler 12 is completed by storing the data related to the audio power and spectral frequency, and their respective flow rates in memory as look-up tables or mathematical expressions, which allows values of audio power or spectral frequency to be input and values of flow rate to be output.

The method for obtaining a flow profile for the inhaler 12 in use is now described with reference to FIGS. 6 and 7.

The mobile device 10 is placed proximate the inhaler device 12 (e.g., approximately 0.5 m apart). The user is asked to use the inhaler 12 in the usual manner by drawing air through the inhaler device 12. While the user draws air through the device, the processor 14 of the device 10 detects and samples the acoustic sound emission produced by the inhaler 12, which is stored in the memory 18. The processor 14 optionally averages the power spectrum using known techniques.

Figure 6:
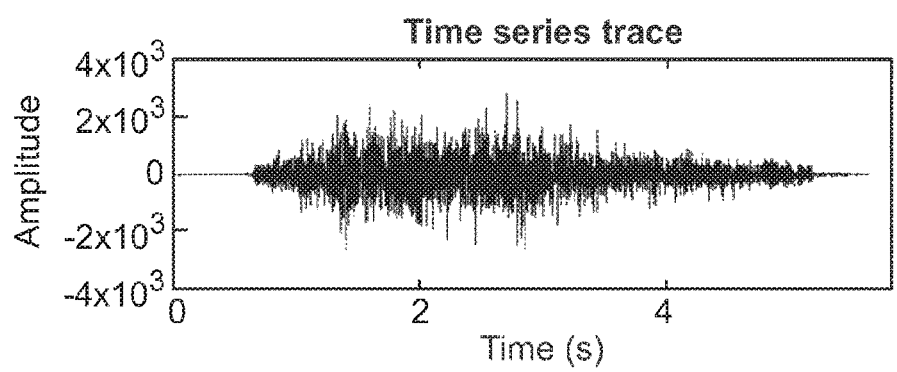
FIG. 6 illustrates a graph of measured data from a microphone (upper graph) and a spectrogram generated from the measure data (lower graph)
Figure 6:
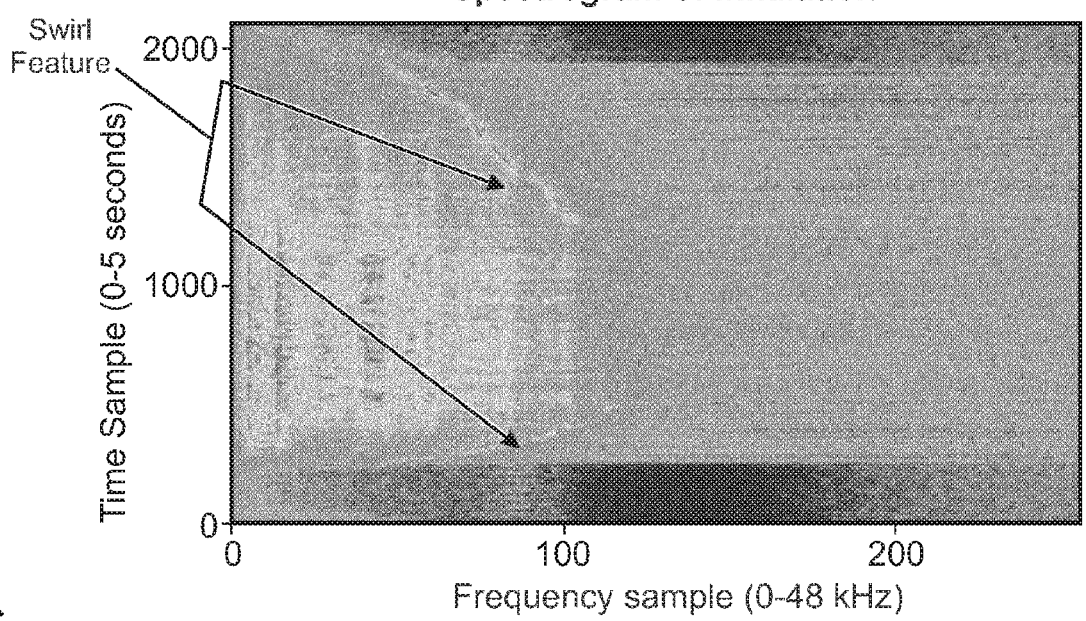

FIG. 6 (upper graph) is a time series trace of the amplitude of the signal measured using the microphone against time as a user draws air through the inhaler device 12 in the usual manner over a time of 6 seconds. In the upper graph of FIG. 6, the y-axis is the signal amplitude in arbitrary units when sampled by the processor 14 and is representative of a constant multiplied by the microphone voltage. The lower graph in FIG. 6 is a spectrogram that has been obtained from the time series trace illustrated in the upper graph of FIG. 6 using the techniques described above (i.e., FFT in time). The swirl features are illustrated in the lower graph of FIG. 6. In the lower graph of FIG. 6, the y-axis is time during the recording of the inhalation from 0 to 5 seconds at sample periods of 2.67 ms, and the x-axis is frequency from 0 to 48 kHz at sample periods of 187.5 Hz.

The processor 14 subsequently estimates the acoustic power within a pass band having a spectral width of 8 kHz at a centre frequency of 5 kHz. The filtered signal is subsequently sampled over 80 ms blocks with a 50% overlap to obtain a 25 Hz update rate. The processor 14 subsequently detects the spectral frequency (i.e., the spectral peaks) of the swirl tones of the signal at 25 Hz intervals and converts these to flow rates using the predetermined expression or look-up table for flow rates. It will be appreciated that in this example flow rates of less than 25 litres per minute (i.e., the low flow rates) are determined using the spectral peaks. The spectral peaks are estimated using the median filtering and thresholding, as is described above for the calibration process. This is to say that the largest spectral peak in the range of frequencies, for example, 5 kHz to 20 kHz is identified. It will be appreciated that it may not be possible to identify a spectral peak in a sampled time period, but if this is the case, it should be possible to identify at least one spectral peak over the extent of the times series data.

The processor 14 subsequently uses the expression or look-up table of acoustic power values to convert the detected acoustic power to flow rates. The flow rates obtained using the acoustic power measurements are subsequently adjusted, or calibrated, as appropriate using the flow rates obtained using the spectral frequency of the swirl tones. For example, the processor 14 determines the flow rate for a specified sample obtained at selected time. The acoustic power at the same selected time and its associated flow rate is obtained from the look-up table of acoustic power values. If the acoustic power flow rate does not equal the spectral peak flow rates, within a predetermined tolerance (e.g., 5%), an adjustment factor for the acoustic power flow rate is determined, and is applied to all of the previously converted acoustic power flow rates. The adjustment may involve addition, subtraction, multiplication or division or any combination thereof. The adjustment value is typically an acoustic power value in dB such that it is subtracted or added to the acoustic power values. This process may be repeated for all of the detected spectral peak flow rates, and the adjustment factor obtained for each spectral peak flow rate may be combined. Once the acoustic power flow rates have been adjusted (i.e., calibrated), a report of flow rate against time can be generated in the form of a graph for example. This is referred to as a flow profile.

In the example described above, it is assumed that only a single spectral peak is detected when the method described herein is used to produce a flow profile. However, it is possible that multiple spectral peaks may be detected. If multiple spectral speaks are detected (i.e., multiple time periods within the sample data from the microphone are determined to include a spectral peak) the (linear) implied powers for each of the spectral peaks are summed and the corresponding measured audio powers are summed and a ratio is taken therefrom. The acquired ratio is subsequently converted to decibels to give the calibration offset. The implied power is determined by estimating the flow that corresponds to the swirl frequency peak, and then estimating the audio power based on the audio power versus flow rate data/look-up from the calibration stage. It will be appreciated that the same technique is used if a single spectral peak is detected, but it will not be necessary to sum any values.

Figure 7:
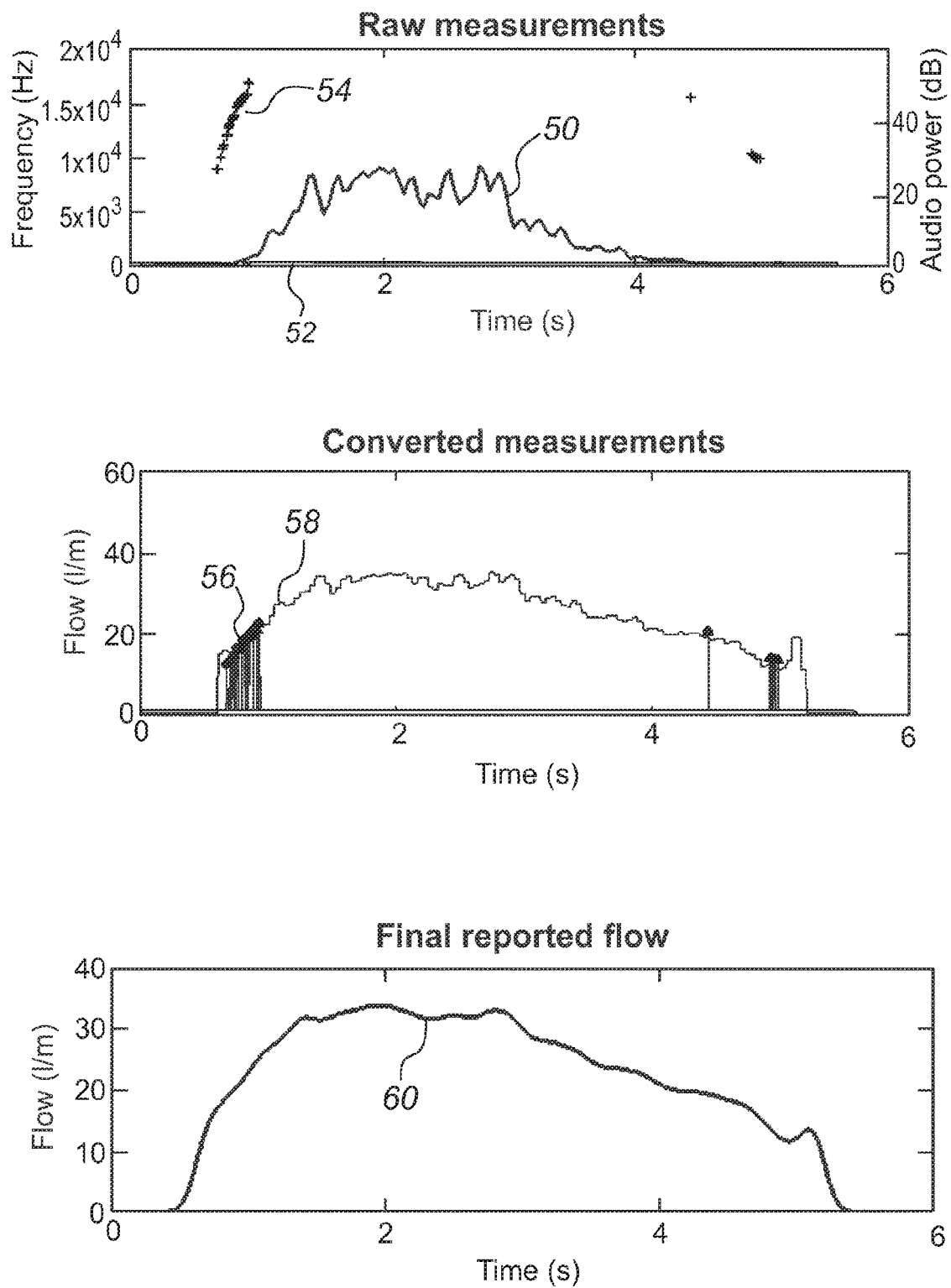
FIG. 7 graphically illustrates a method shown in a flow chart of FIG. 8.

FIG. 8 is a flow chart 30 depicting a method performed by the processor 14 of the mobile device 10, which is now described in association with FIG. 7. FIG. 7 graphically illustrates the method shown in the flow chart of FIG. 8. The steps may be performed in a different order than illustrated, and one or more steps may be optional.

At block 32, the device 10 detects and samples the acoustic sound emission produced by the inhaler 12, whilst a user draws air through the inhaler 12.

At block 34, the device 10 estimates the acoustic power using a spectral width of 8 kHz at a centre frequency of 5 kHz. This is illustrated in FIG. 7 as line 50. The device 10 may optionally average the power spectrum for each sample point.

At block 36, the device 10 samples the filter signal over 80 ms blocks with a 50% overlap to obtain a 25 Hz update rate. This is illustrated in FIG. 7 as line 52.

At block 38, the device 10 detects the spectral frequency of the swirl tones (see FIG. 7, crosses 54) and converts these to flow rates using the predetermined expression or look-up table for flow rates less than 25 litres per minute, for example (i.e., the low flow rates). The converted flow rates obtained from the spectral frequency of the swirl tones are illustrated in FIG. 7 as crosses 56.

At block 40, the device 10 converts the detected acoustic power to flow rates using the expression or look-up table of acoustic power values. This is illustrated in FIG. 7 as line 58.

At block 42, the device 10 calibrates the flow rates obtained using the acoustic power measurements according to the flow rates obtained using the spectral frequency of the swirl tones.

At block 44, the device 10 generates and outputs a flow profile of flow rate against time. This is illustrated in FIG. 7 as line 60.

Thus, the method described herein simplifies the calibration process, whilst retaining the ability to make accurate measurements. Moreover, any modification to the inhaler is reduced or eliminated.

In the embodiment described above, all of the processing including the initial calibration is performed on a single mobile device. However, it will be appreciated that the mobile device 12 may be used only to sample the acoustic sound emission from the inhaler 12, which is subsequently transmitted to a general purpose computer, for example using WiFi, whereby the processing is performed by the general purpose computer. The mobile device 10 may receive the flow profile data for display on its display 16. The general purpose computer may be at the same location as the mobile device 10 user, or may be remotely located elsewhere, for example. Moreover, a discrete microphone connected to a general purpose computer or the mobile device 10 may be used to sample the acoustic sound emission from the inhaler 12, and the microphone may be optionally fixed to the inhaler 12 using a mechanical fixing or constraint, or a suitable adhesive. If using a microphone fixed to the inhaler 12, it may be a wireless enabled (e.g., WiFi or Bluetooth®) or wired microphone to enable it to communicate with the processing device.

FIG. 9 illustrates a series of graphs which may be obtained when the method described above is performed using a smartphone and an application running thereon to sample the acoustic sound emissions produced by the inhaler 12 during normal use. The sampled data was subsequently transmitted to a general purpose computer for processing. The upper graph represents the data received from the smartphone after it has been filtered and sampled. In the upper graph, the solid line 62 is the audio power and the crosses 64 are the detected spectral peaks. The central graph represents the flow rates obtained from the spectral peaks (crosses 66) and the flow rates obtained from the acoustic power and converted/calibrated using the spectral peaks (solid line 68). Finally, the lower graph is the reported flow profile (solid line 70).

The method of generating a flow profile of the inhalation device may be used to monitor the use of an inhalation device, for example. In this regard, a user is instructed to inhale air through an inhalation device and a flow profile is generated, as is discussed above. The flow profile is then stored and or transmitted elsewhere for assessment or comparison with previous/future flow profiles or a preferred (i.e., "ideal") flow profile. Moreover, a user may be trained to use an inhalation device based on a generated flow profile. For example, a user is instructed to inhale air through an inhalation device and a flow profile is generated. A practitioner subsequently displays the flow profile and determines any portions or sections of the flow profile that could be improved and communicates these to the user. It will be appreciated that this form of training or monitoring could be used by a practitioner remotely located with respect to the user.

The examples described herein refer to specific ranges and values. However, it will be apparent to the skilled person that these are only examples and should not be considered to limit the invention. For example, the inhaler device has been calibrated herein with a flow rate of up to 60 litres per minute (approximately 0.001 m$^3$/s), but it will be appreciated that the calibration may be performed with greater flow rates of up to 200 litres per minute (approximately 0.0033 m$^3$/s), for example, and specifically 120 litres per minute (approximately 0.002 m$^3$/s). These calibrated values can then be used to produce a flow profile with greater flow rates.

The embodiments described in accordance with the present invention may be provided as a computer software product. The computer software product may be provided in, on or supported by a computer readable medium which could be provided as all possible permanent and non-permanent forms of computer readable medium either transitory in nature, such as in a data transmission signal for example sent over the internet, or non-transitory in nature such as in the memory 18 of the device 10 or other, non-volatile storage such as memory. On the other hand the computer readable medium may be a non-transitory computer readable medium comprising all computer-readable media.

The term "computer readable medium" (or non-transitory computer readable medium) as used herein means any medium which can store instructions for use by or execution by a computer or other computing device including, but not limited to, a portable computer diskette, a hard disk drive (HDD), a random access memory (RAM), a read-only memory (ROM), an erasable programmable-read-only memory (EPROM) or flash memory, an optical disc such as a Compact Disc (CD), Digital Versatile Disc (DVD) or Blu-ray™ Disc, and a solid state storage device (e.g., NAND flash or synchronous dynamic RAM (SDRAM)).

It will be appreciated that the foregoing discussion relates to particular embodiments. However, in other embodiments, various aspects and examples may be combined.

The invention claimed is:

1. A method for generating a flow profile of an inhalation device, comprising the steps of:
   providing an inhalation device and a processor in communication with a microphone;
   instructing a user to inhale air through an inhalation device so as to induce acoustic emissions;
   measuring acoustic emissions induced by the user's inhalation flow through the inhalation device using the microphone and communicating acoustic emissions information from the microphone to the processor;
   detecting two or more peak frequencies in the measured acoustic emissions with the processor;
   detecting acoustic power of the measured acoustic emissions with the processor; and
   generating a flow profile based on the detected peak frequencies and the detected acoustic power, wherein each of the flow rates of the flow profile determined based on the detected acoustic power are compared and calibrated according to one or more flow rates determined based on the detected peak frequencies;
   displaying the flow profile;
   determining any portions of the flow profile that require improvement; and
   communicating any improvements to the user.

2. The method of claim 1, wherein each of the peak frequencies represents a spectral peak of an air flow through the inhalation device at a predetermined flow rate.

3. The method of claim 1, wherein the acoustic emissions are measured over a predetermined period of time and the two or more peak frequencies are detected at regular intervals over the predetermined period of time.

4. The method of claim 1, wherein the flow profile is generated using a predetermined relationship between the two or more peak frequencies and respective flow rates through the inhalation device.

5. The method of claim 4, wherein the predetermined relationship is represented by a look-up table.

6. A method for generating a flow profile of an inhalation device, comprising the steps of:
   providing an inhalation device and a processor in communication with a microphone;
   instructing a user to inhale air through an inhalation device so as to induce acoustic emissions;
   measuring acoustic emissions induced by the user's inhalation flow through the inhalation device using the microphone and communicating acoustic emissions information from the microphone to the processor;
   detecting one or more peak frequencies in the measured acoustic emissions with the processor;
   detecting acoustic power of the measured acoustic emissions with the processor; and
   generating a flow profile based on the detected acoustic power and the detected peak frequencies, wherein each of the flow rates of the flow profile determined based on the detected acoustic power are compared and calibrated according to one or more flow rates determined based on the detected peak frequencies;
   displaying the flow profile;
   determining any portions of the flow profile that require improvement; and
   communicating any improvements to the user.

7. The method of claim 6, wherein the acoustic emissions are measured over a predetermined period of time and the one or more peak frequencies and the acoustic power are detected at regular intervals over the predetermined period of time.

8. The method of claim 6, wherein the flow profile is generated using predetermined relationships between the one or more peak frequencies and respective flow rates through the inhalation device, and acoustic power and respective flow rates through the inhalation device.

9. The method of claim 8, wherein the predetermined relationship is represented by a look-up table.

10. The method of claim 6, wherein the acoustic power is detected within a predetermined frequency band.

11. The method of claim 6, wherein each of the peak frequencies represents a spectral peak of an air flow through the inhalation device at a predetermined flow rate.

12. A computer program product having instructions stored thereon which when executed on a processor performs the method according to claim 1.

13. A system for generating a flow profile comprising:
an inhalation device;
a processor in communication with a microphone, wherein the microphone is configured to detect acoustic emissions from the inhalation device;
an input/output interface for sending information to and from the processor;
a display; and
a memory unit for storing information from the processor;
wherein the processor is configured to:
receive acoustic emissions information from the microphone;
detect two or more peak frequencies in the measured acoustic emissions;
detect acoustic power of the measured acoustic emissions;
generate a flow profile for the inhalation device based on the detected peak frequencies and the detected acoustic power;
display the flow profile; and
store the flow profile in the memory unit,
wherein the processor is further configured to determine any portions of the flow profile that require improvement and communicate any improvements to a user via the display, and
wherein each of the flow rates of the flow profile determined based on the detected acoustic power are compared and calibrated according to one or more flow rates determined based on the detected peak frequencies.

14. A system for generating a flow profile comprising:
an inhalation device;
a processor in communication with a microphone, wherein the microphone is configured to detect acoustic emissions from the inhalation device;
an input/output interface for sending information to and from the processor;
a display; and
a memory unit for storing information from the processor;
wherein the processor is configured to:
receive acoustic emissions information from the microphone;
detect one or more peak frequencies in the measured acoustic emissions;
detect acoustic power of the measured acoustic emissions;
generate a flow profile for the inhalation device based on the detected acoustic power and the detected one or more peak frequencies, and
display the flow profile;
wherein the processor is further configured to determine any portions of the flow profile that require improvement and communicate any improvements to a user via the display, and
wherein each of the flow rates of the flow profile determined based on the detected acoustic power are compared and calibrated according to one or more flow rates determined based on the detected peak frequencies.

15. A mobile device comprising a system according to claim 13.

16. A method of monitoring use of an inhalation device, comprising the steps of:
instructing a user to inhale air through an inhalation device;
performing the method according to claim 1 as the user inhales air through the inhalation device; and
storing the flow profile.

* * * * *